US008415472B2

(12) United States Patent
Chung et al.

(10) Patent No.: US 8,415,472 B2
(45) Date of Patent: Apr. 9, 2013

(54) WATER SOLUBLE PHOTOCHROMIC COMPOUNDS FOR LABELING OF BIOMOLECULES AND METHOD FOR DETECTING BIOMOLECULES USING THE SAME

(75) Inventors: Bony Hyun Chung, Daejeon (KR); Sang Jeon Chung, Daejeon (KR); Suh Hyun Lee, Daejeon (KR); Im Sik Chung, Daejeon (KR); Hyun Kyu Park, Daejeon (KR); Chang Soo Lee, Daejong (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 12/739,601

(22) PCT Filed: Aug. 21, 2008

(86) PCT No.: PCT/KR2008/004882
§ 371 (c)(1),
(2), (4) Date: Jun. 3, 2010

(87) PCT Pub. No.: WO2009/054608
PCT Pub. Date: Apr. 30, 2009

(65) Prior Publication Data
US 2010/0256397 A1    Oct. 7, 2010

(30) Foreign Application Priority Data
Oct. 24, 2007  (KR) ........................ 10-2007-0107245

(51) Int. Cl.
*C07D 237/26* (2006.01)
(52) U.S. Cl. ...................................................... 544/235
(58) Field of Classification Search .................. 548/518; 544/235
See application file for complete search history.

(56) References Cited

U.S. PATENT DOCUMENTS
2003/0213942 A1    11/2003  Kim et al.
2005/0080260 A1     4/2005  Mills et al.

OTHER PUBLICATIONS

King, Med. Chem., (1994) pp. 206-208.*
de Jong et al., Eu. J. Org. Chem. (2003), vol. 10, pp. 1887-1893.*
Hirose, Takashi, et al., Self-Assembly of Photochromic Diarylethenes with Amphiphilic Side Chains: Reversible Thermal and Photochemical Control, J. Org. Chem., Sep. 29, 2006, pp. 7499-7508, vol. 71, No. 20.
Irie, Masahiro, Diarylethenes for Memories and Switches, Chem. Rev., 2000, pp. 1685-1716, vol. 100.
Takeshita, Michinori, et al., Novel saccharide tweezers with a diarylethene photoswitch, Chem. Commun., 1996, pp. 1807-1808.
Mitchell, Reginald H., et al.; "The Effect of Addition of Fluorescent Moieties to Dihydropyrenes: Enhancing Photochromicity and Fluorescence Monitoring," Journal of Organic Chemistry, 2007, pp. 7939-7946, vol. 72.
Morimoto, Masakazu, et al.; "Crystal Engineering of Photochromic Diarylethene Single Crystals," The Chemical Record, 2004, pp. 23-38, vol. 4.
Soh, Nobuaki, et al.; "A fluorescent photochromic compound for labeling biomolecules," Chemical Communications, 2007, pp. 5206-5208, vol. 48.
International Search Report for International Patent Application No. PCT/KR2008/004882, Mar. 9, 2009.

* cited by examiner

*Primary Examiner* — Taofiq A Solola
(74) *Attorney, Agent, or Firm* — Andrew D. Gerschutz; Tristan A. Fuierer; Moore & Van Allen, PLLC

(57) ABSTRACT

The present invention relates to water-soluble photochromic compounds for labeling biomolecules and a method of detecting biomolecules using the same. More specifically, relates to water-soluble photochromic compounds for labeling biomolecules, in which a functional group rendering photochromic molecules water-soluble is linked to a functional group capable of binding to biomolecules, and a method of detecting biomolecules using the same. Because the disclosed water-soluble photochromic compounds exhibit the color corresponding to the wavelength of visible light range, they allow signals to be easily detected not only with an UV-VIS spectrophotometer but also visually. Accordingly, the photochromic compounds can be advantageously used in sensors for diagnosing diseases.

19 Claims, 3 Drawing Sheets

WATER SOLUBLE PHOTOCHROMIC COMPOUNDS FOR LABELING OF BIOMOLECULES AND METHOD FOR DETECTING BIOMOLECULES USING THE SAME

CROSS-REFERENCE TO RELATED APPLICATIONS

This application is filed under the provisions of 35 U.S.C. §371 and claims the priority of International Patent Application No. PCT/KR2008/004882 filed on 21 Aug. 2008 entitled "Water Soluble Photochromic Compounds for Labeling of Biomolecules and Method for Detecting Biomolecules Using the Same" in the name of Bong Hyun CHUNG, et al., which claims priority to Korean Patent Application No. 10-2007-0107245 filed on 24 Oct. 2007, both of which are hereby incorporated by reference herein in their entirety.

TECHNICAL FIELD

The present invention relates to water-soluble photochromic compounds for labeling biomolecules and a method of detecting biomolecules using the same, and more particularly to water-soluble photochromic compounds for labeling biomolecules, in which a functional group rendering photochromic molecules water-soluble is linked to a functional group capable of binding to biomolecules, and a method of detecting biomolecules using the same.

BACKGROUND ART

Photochromism refers to the phenomenon that the color of either compounds, which change color when exposed to UV or visible light, or products containing such compounds, show a reversible color change by light. Photochromic compounds exist in at least two isomeric forms having different physical properties such as absorption properties and refractivity and can be transformed from one form to another form by light excitations at prescribed wavelengths.

Photochromic materials which can show a reversible color change by light are applicable in various fields, including photorecorders, photoswitches and modulators. For example, diarylethene compounds change color when exposed to UV light, and then return to their original color when irradiated with light of a different wavelength. Since such compounds were synthesized for the first time in the year 1985, they have been known to be stable photochromic compounds which do not exhibit any heat-induced color change after being exposed to light. In addition, various types of derivatives have been synthesized, and among them, diarylethene compounds substituted with fluorine are known to show high stability and very fast photochromism (Takeshita, M. et al., *Chem. Commun.*, 1807, 1996; Irie, M., *Chem. Rev.*, 1685, 1996).

Meanwhile, diarylethene compounds are soluble in most organic solvents, but are poorly soluble in water. For this reason, the application thereof in the biological field which is based on the aqueous solution phase is extremely limited. Recently, there was a report that diarylethene compounds can be converted to water-soluble compounds by introducing ethylene glycol thereinto (Hirose, T. et al., *J. Org. Chem.*, 7499, 2006). In addition, Japanese Patent Publication No. 2003-246776 discloses a method of crosslinking biomolecules having a photochromic molecule and a thiol group with a maleimide group in order to provide cross-linkable photochromic molecules, which are obtained by reversibly changing the structure of biofunctional molecules, and to provide biofunctional molecule derivatives capable of producing mechanical energy. However, such molecules are difficult to apply in the biological field, because they are not water-soluble photochromic molecules.

Accordingly, there is an urgent need to develop biomolecule detection technology which can easily detect signals not only with an UV-VIS spectrophotometer but also visually using photochromic compounds showing a reversible color change by light of specific wavelengths, and which can reduce undesired background signals to greatly improve detection sensitivity.

The present inventors have prepared water-soluble photochromic compounds by linking a functional group rendering photochromic molecules water-soluble to a functional group capable of covalently bonding to biomolecules and have found that, when the prepared water-soluble photochromic compounds are labeled to biomolecules, such as proteins, nucleic acids or the like, the photochromic compounds labeled to the biomolecules generate color change-inducing signals by light of specific wavelengths, such that signals can be detected even visually without using a separate device, and the detection sensitivity of biomolecules to be measured can be greatly improved, thereby completing the present invention.

SUMMARY OF INVENTION

It is an object of the present invention to provide water-soluble photochromic compounds for labeling biomolecules, in which a functional group rendering photochromic molecules water-soluble is linked to a functional group capable of covalently bonding to biomolecules, and a preparation method thereof.

Another object of the present invention is to provide a method of detecting biomolecules using said water-soluble photochromic compounds for labeling biomolecules.

To achieve the above objects, the present invention provides water-soluble photochromic compounds for labeling biomolecules, which are represented by the following formula 1:

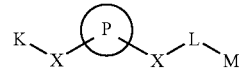

[Formula 1]

wherein, P is a photochromic molecule, L is an atom or an atomic group (except a hydrogen atom (H)), a peptide-, DNA-, PNA-, protein- or nucleic acid-binding ligand, an alkyl having 1 to 100 carbon atoms, an aryl having 6 to 100 carbon atoms, a heterocyclic linker having 2 to 100 carbon atoms, or $(CH_2CH_2O)_n$, where n is an integer ranging from 1 to 100, M is a functional group binding selectively to biomolecules, K is a fluorescent substance or an L-, L-M- or L-M-fluorescent substance, and X is a functional group for linking K or L to P.

The present invention also provides fluorescence switching compounds for labeling biomolecules which are represented by the following formula 2:

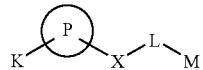

[Formula 2]

wherein, P is a photochromic molecule, L is an atom or an atomic group (except a hydrogen atom (H)), a peptide-, DNA-, PNA-, protein- or nucleic acid-binding ligand, an alkyl having 1 to 100 carbon atoms, an aryl having 6 to 100 carbon atoms, a heterocyclic linker having 2 to 100 carbon atoms, or $(CH_2CH_2O)_n$, where n is an integer ranging from 1 to 100, M is a functional group binding selectively to biomolecules, K is a fluorescent substance or an L-fluorescent substance, and X is a functional group for linking L to P.

The present invention also provides water-soluble photochromic compounds for labeling biomolecules which are represented by the following formula 12:

[Formula 12]

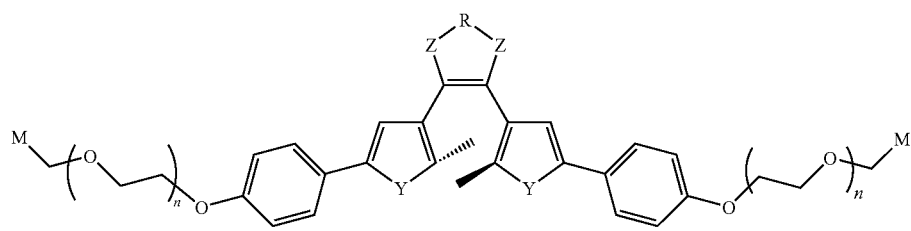

wherein R is a bond or a $C_1$-$C_3$ alkylene group which is unsubstituted or substituted with an oxygen or fluorine atom, Y is independently an oxygen, nitrogen or sulfur atom, Z is a methylene group or a carbonyl group, which are unsubstituted or substituted with fluorine, M is a functional group binding selectively to biomolecules, and n is an integer ranging from 1 to 100.

The present invention also provides a method for preparing water-soluble photochromic compounds for labeling biomolecules, which are represented by formula 1:

[Formula 1]

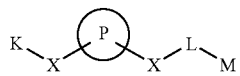

wherein P is a photochromic molecule, L is an atom or an atomic group (except a hydrogen atom (H)), a peptide-, DNA-, PNA-, protein- or nucleic acid-binding ligand, an alkyl having 1 to 100 carbon atoms, an aryl having 6 to 100 carbon atoms, a heterocyclic linker having 2 to 100 carbon atoms, or $(CH_2CH_2O)_n$, where n is an integer ranging from 1 to 100, M is a functional group binding selectively to biomolecules, K is a fluorescent substance or an L, L-M or L-M-fluorescent substance, and X is a functional group for linking K or L to P, the method comprising the steps of:

(a) allowing a photochromic molecule (P) containing, at one end or both ends thereof a functional group selected from the group consisting of a hydroxyl group (—OH), a thiol group (—SH), a methyl group (—CH$_3$), an amine group (—NH$_2$) and combinations thereof to react with an end-modified oligo(ethylene glycol) represented by the following formula 11 in the presence of a base, thus preparing an end-group-protected intermediate represented by the following formula 20:

[Formula 11]

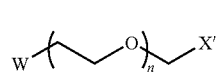

wherein W is tosylate (—OTs), mesylate (—OMs) or triflate (—OTf), X' is carboxylic acid alkyl ester (C(=O)OR', R'=$C_1$-$C_4$ alkyl), azide (N$_3$) or carbamate (NHC(O)OR), where R is t-butyl, benzyl or methyl, and n is an integer ranging from 1 to 100,

[Formula 20]

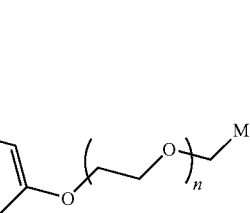

wherein P is a photochromic molecule, X' is carboxylic acid alkyl ester (C(=O)OR', R'=$C_1$-$C_4$ alkyl), azide (N$_3$) or carbamate (NHC(O)OR), where R is t-butyl, benzyl or methyl, and n is an integer ranging from 1 to 100;

(b) subjecting the end group-protected intermediate represented by formula 20 to ester hydrolysis or azide reduction in the presence of a base and solvent, thus preparing a carboxylic acid intermediate or an amine intermediate; and (c) either allowing the prepared carboxylic acid intermediate to react with NHS/EDC or NHS—SO$_3$Na so as to convert the carboxylic acid intermediate to N-hydroxysuccinic acid imide or N-hydroxysulfo-succinic acid imide derivatives as photochromic compounds for labeling biomolecules, or allowing the prepared amine intermediate to react with a compound selected from the group consisting of carbonyldimidazole, carbonyldisuccinate, phosgene and ammonium thiocyanate so as to convert the amine intermediate to isocyanate or isothiocyanate derivatives as photochromic compounds for labeling biomolecules.

The present invention also provides a method for preparing water-soluble photochromic compounds for labeling biomolecules, which are represented by formula 12:

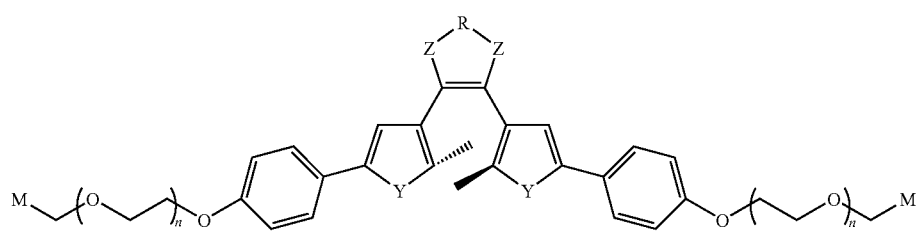

[Formula 12]

wherein R is a bond or a $C_1$-$C_3$ alkylene group which is unsubstituted or substituted with an oxygen or fluorine atom, Y is independently an oxygen, nitrogen or sulfur atom, Z is a methylene group or a carbonyl group, which are unsubstituted or substituted with fluorine, M is a functional group binding selectively to biomolecules, and n is an integer ranging from 1 to 100, the method comprising the steps of:

(a) allowing a photochromic molecule, containing a hydroxyl group (—OH) at both ends thereof and represented by the following formula 3', to react with an end-modified oligo(ethylene glycol) represented by the following formula 11 in the presence of a base, thus preparing an end group-protected intermediate represented by the following formula 14:

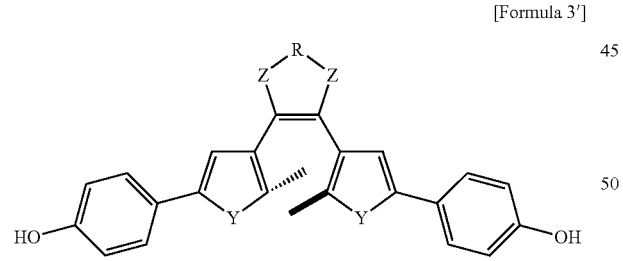

[Formula 3']

wherein R is a bond or a $C_1$-$C_3$ alkylene group which is unsubstituted or substituted with an oxygen or fluorine atom, Y is independently an oxygen, nitrogen or sulfur atom, Z is a methylene group or a carbonyl group, which are unsubstituted or substituted with fluorine,

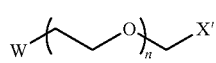

[Formula 11]

wherein W is tosylate (—OTs), mesylate (—OMs) or triflate (—OTf), X' is carboxylic acid alkyl ester (C(═O) OR', R'═$C_1$-$C_4$ alkyl), azide ($N_3$) or carbamate (NHC (O)OR), where R is t-butyl, benzyl or methyl, and n is an integer ranging from 1 to 100,

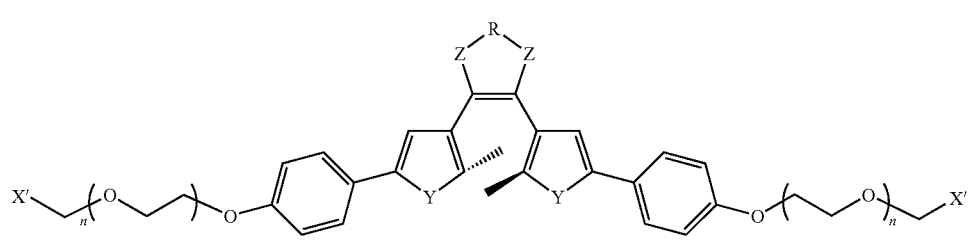

[Formula 14]

wherein R is a bond or a $C_1$-$C_3$ alkylene group which is unsubstituted or substituted with an oxygen or fluorine atom, Y is independently an oxygen, nitrogen or sulfur atom, Z is a methylene group or a carbonyl group, which are unsubstituted or substituted with fluorine, X' is carboxylic acid alkyl ester (C(═O)OR', R'═$C_1$-$C_4$ alkyl), azide ($N_3$) or carbamate (NHC(O)OR), where R is t-butyl, benzyl or methyl, and n is an integer ranging from 1 to 100;

(b) subjecting the end group-protected intermediate represented by formula 14 to ester hydrolysis or azide reduction in the presence of a base and solvent, thus preparing a carboxylic acid intermediate or an amine intermediate; and (c) either allowing the prepared carboxylic acid intermediate to react with NHS/EDC or NHS—$SO_3$Na so as to convert the carboxylic acid intermediate to N-hydroxysuccinic acid imide or N-hydroxysulfo-succinic acid imide derivatives as photochromic compounds for labeling biomolecules, or allowing the prepared amine intermediate to react with a compound selected from the group consisting of carbonyldimidazol, carbonyldisuccinate, phosgene and ammonium thiocyanate so as to convert the amine intermediate to isocyanate or isothiocyanate derivatives as photochromic compounds for labeling biomolecules.

The present invention also provides a method for labeling or detecting biomolecules, which is characterized by using either said water-soluble photochromic compounds for labeling biomolecules or said fluorescence switching compounds.

Other features and aspects of the present invention will be apparent from the following detailed description and the appended claims.

BRIEF DESCRIPTION OF DRAWINGS

In FIG. 5, (a) shows the strip sensor before irradiation with UV light, and (b) shows the strip sensor after irradiation with UV light.

DETAILED DESCRIPTION OF THE INVENTION, AND PREFERRED EMBODIMENTS

Figure 1:
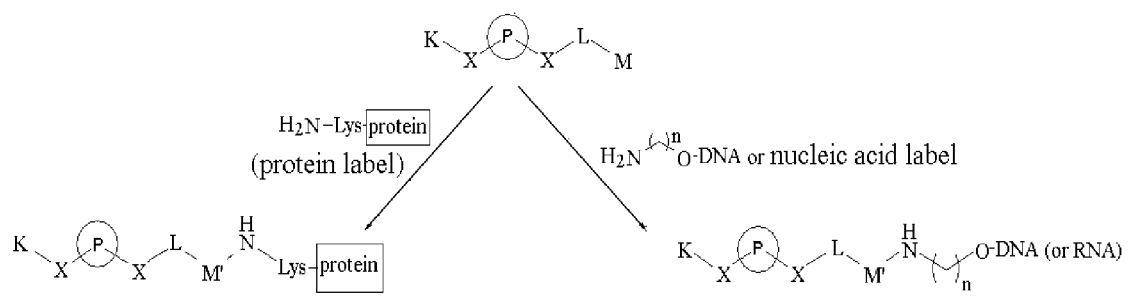
FIG. 1 schematically shows a method of labeling biomolecules with water-soluble photochromic compounds for labeling biomolecules according to the present invention.

In one aspect, the present invention relates to water-soluble photochromic compounds for labeling biomolecules, which are represented by the following formula 1; and method for preparing the same:

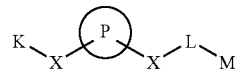

[Formula 1]

wherein P is a photochromic molecule, L is an atom or an atomic group (except a hydrogen atom (H)), a peptide-, DNA-, PNA-, protein- or nucleic acid-binding ligand, an alkyl having 1 to 100 carbon atoms, an aryl having 6 to 100 carbon atoms, a heterocyclic linker having 2 to 100 carbon atoms, or $(CH_2CH_2O)_n$, where n is an integer ranging from 1 to 100, M is a functional group binding selectively to biomolecules, K is a fluorescent substance or an L, L-M or L-M-fluorescent substance, X is a functional group for linking K or L to P, and X is preferably selected from the group consisting of O, S, NH, and $CH_2$.

Photochromic molecules

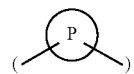

according to the present invention may be selected from among, but not limited to, the compounds shown in Table 1.

TABLE 1

| isomer A | isomer B |
|---|---|
| Formula 3 | |
| Formula 4 | |
| Formula 5 | |
| Formula 6 | |

TABLE 1-continued

| isomer A | isomer B |
|---|---|
| Formula 7 | |
| Formula 8 | |
| Formula 9 | |
| Formula 10 | |

In the formula 3 and 4, R is a bond or a $C_1$-$C_3$ alkylene group which is unsubstituted or substituted with an oxygen or fluorine atom, Y is independently an oxygen, nitrogen or sulfur atom, and Z is a methylene group or a carbonyl group, which are unsubstituted or substituted with fluorine.

In the present invention, the functional group (M) binding to biomolecules is preferably selected from the group consisting of a carboxyl group, a carboxyl acid derivative (C(=O)—Cl, C(=O)—Br, or C(=O)—O-succinimide), an isocyanate group, an isothiocyanate group, an amine group, a thiol group, a hydroxyl group, an iodoacetamino group, an α-haloacetyl group and a maleimide group.

The water-soluble photochromic compounds for labeling biomolecules, which are represented by formula 1 according to the present invention is preferably prepared by the following steps:

(a) allowing a photochromic molecule (P) containing at one end or both ends thereof a functional group selected from the group consisting of a hydroxyl group (—OH), a thiol group (—SH), a methyl group (—CH₃), an amine group (—NH₂) and combinations thereof to react with an end-modified oligo(ethylene glycol) represented by the following formula 11 in the presence of a base, thus preparing an end-group-protected intermediate represented by the following formula 20:

[Formula 11]

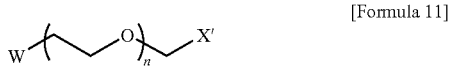

wherein W is tosylate (—OTs), mesylate (—OMs) or triflate (—OTf), X' is carboxylic acid alkyl ester (C(=O)OR', R'=$C_1$-$C_4$ alkyl), azide ($N_3$) or carbamate (NHC(O)OR), where R is t-butyl, benzyl or methyl, and n is an integer ranging from 1 to 100,

[Formula 20]

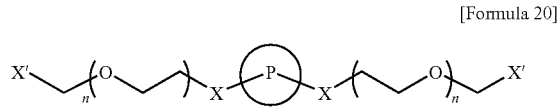

wherein P is a photochromic molecule, X' is carboxylic acid alkyl ester (C(=O)OR', R'=C₁-C₄ alkyl), azide (N₃) or carbamate (NHC(O)OR), where R is t-butyl, benzyl or methyl, and n is an integer ranging from 1 to 100;

(b) subjecting the end group-protected intermediate represented by formula 20 to ester hydrolysis or azide reduction in the presence of a base and solvent, thus preparing a carboxylic acid intermediate or an amine intermediate; and (c) either allowing the prepared carboxylic acid intermediate to react with NHS/EDC or NHS—SO₃Na so as to convert the carboxylic acid intermediate to N-hydroxysuccinic acid imide or N-hydroxysulfosuccinic acid imide derivatives as photochromic compounds for labeling biomolecules, or allowing the prepared amine intermediate to react with a compound selected from the group consisting of carbonyldimidazol, carbonyldisuccinate, phosgene and ammonium thiocyanate so as to convert the amine intermediate to isocyanate or isothiocyanate derivatives as photochromic compounds for labeling biomolecules.

In another aspect, the present invention relates to water-soluble photochromic compounds for labeling biomolecules, which are represented by formula 12; and a method for preparing the same:

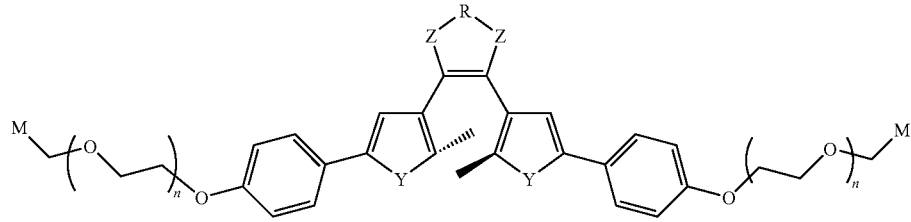

[Formula 12]

wherein R is a bond or a C₁-C₃ alkylene group which is unsubstituted or substituted with an oxygen or fluorine atom, Y is independently an oxygen, nitrogen or sulfur atom, Z is a methylene group or a carbonyl group, which are unsubstituted or substituted with fluorine, M is a functional group binding selectively to biomolecules, and n is an integer ranging from 1 to 100.

The water-soluble photochromic compounds for labeling biomolecules, which are represented by formula 12 according to the present invention is preferably prepared by following steps:

(a) allowing a photochromic molecule, containing a hydroxyl group (—OH) at both ends thereof and represented by the following formula 3', to react with an end-modified oligo(ethylene glycol) represented by the following formula 11 in the presence of a base, thus preparing an end group-protected intermediate represented by the following formula 14:

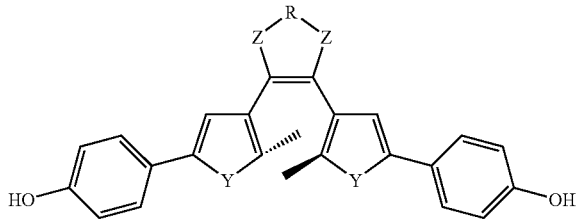

[Formula 3']

wherein R is a bond or a C₁-C₃ alkylene group which is unsubstituted or substituted with an oxygen or fluorine atom, Y is independently an oxygen, nitrogen or sulfur atom, Z is a methylene group or a carbonyl group, which are unsubstituted or substituted with fluorine,

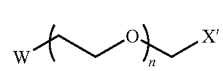

[Formula 11]

wherein W is tosylate (—OTs), mesylate (—OMs) or triflate (—OTf), X' is carboxylic acid alkyl ester (C(=O)OR', R'=C₁-C₄ alkyl), azide (N₃) or carbamate (NHC(O)OR), where R is t-butyl, benzyl or methyl, and n is an integer ranging from 1 to 100,

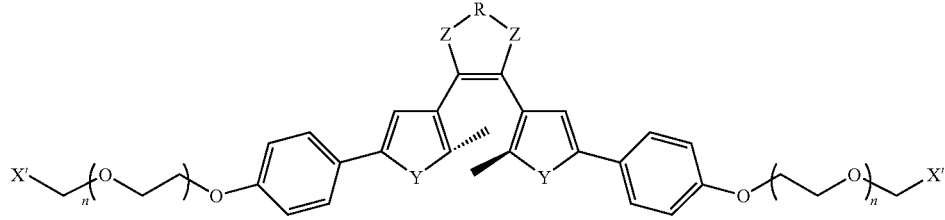

[Formula 14]

wherein R is a bond or a $C_1$-$C_3$ alkylene group which is unsubstituted or substituted with an oxygen or fluorine atom, Y is independently an oxygen, nitrogen or sulfur atom, Z is a methylene group or a carbonyl group, which are unsubstituted or substituted with fluorine, X' is carboxylic acid alkyl ester (C(=O)OR', R'=$C_1$-$C_4$ alkyl), azide ($N_3$) or carbamate (NHC(O)OR), where R is t-butyl, benzyl or methyl, and n is an integer ranging from 1 to 100;

(b) subjecting the end group-protected intermediate represented by formula 14 to ester hydrolysis or azide reduction in the presence of a base and solvent, thus preparing a carboxylic acid intermediate or an amine intermediate; and (c) either allowing the prepared carboxylic acid intermediate to react with NHS/EDC or NHS—$SO_3Na$ so as to convert the carboxylic acid intermediate to N-hydroxysuccinic acid imide or N-hydroxysulfosuccinic acid imide derivatives as photochromic compounds for labeling biomolecules, or allowing the prepared amine intermediate to react with a compound selected from the group consisting of carbonyldimidazol, carbonyldisuccinate, phosgene and ammonium thiocyanate so as to convert the amine intermediate to isocyanate or isothiocyanate derivatives as photochromic compounds for labeling biomolecules.

In still another aspect, the present invention relates to fluorescence switching compounds which are represented by the following formula 2:

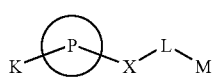

[Formula 2]

wherein P is a photochromic molecule, L is an atom or an atomic group (except a hydrogen atom (H)), a peptide-, DNA-, PNA-, protein- or nucleic acid-binding ligand, an alkyl having 1 to 100 carbon atoms, an aryl having 6 to 100 carbon atoms, a heterocyclic linker having 2 to 100 carbon atoms, or $(CH_2CH_2O)_n$, where n is an integer ranging from 1 to 100, M is a functional group binding selectively to biomolecules, K is a fluorescent substance or an L-fluorescent substance, and X is a functional group for linking L to P.

In the present invention, the functional group (M) binding to biomolecules is preferably selected from the group consisting of a carboxyl group, a carboxyl acid derivative (C(=O)—Cl, C(=O)—Br, or C(=O)—O-succinimide), an isocyanate group, an isothiocyanate group, an amine group, a thiol group, a hydroxyl group, an iodoacetamino group, an α-haloacetyl group and a maleimide group.

In the present invention, the base is preferably selected from the group consisting of, but not limited to, sodium carbonate, potassium carbonate, cesium carbonate, sodium hydrogen carbonate, potassium hydrogen carbonate, sodium hydroxide, potassium hydroxide, triethylamine, DBU, DABCO, DMAP and Proton Sponge. The solvent is preferably selected from the group consisting of, but not limited to, acetonitrile, acetone, methanol, tetrahydrofuran, dioxane, dimethylacetamide, dimethylformamide, N-methylpyrrolidone, dimethylsulfoxide, and a mixture thereof. Also, the method according to the present invention may additionally comprise a step of linking a fluorescent substance to the water-soluble photochromic compounds for labeling biomolecules prepared in step (b).

In the present invention, the fluorescent substance is preferably one or more selected from the group consisting of Alexa 555, Bodipy TMR, Cy3, DY500, Rhodamine red-X, Spectrum orange, Fluorescein isothiocyanate (FITC) or Tetramethylrhodamine isothiocyanate (TRITC), Alexa fluor, Texas red, Tetramethylrhodamine, Cascade blue, DAPI (4',6-diamidino-2-phenylindole), Coumarine, Lucifer yellow and Dansylamide.

In still another aspect, the present invention relates to a method for labeling or detecting biomolecules, which is characterized by using either said water-soluble photochromic compounds for labeling biomolecules or said fluorescence switching compounds.

Hereinafter, the present invention will be described in detail with reference to the accompanying drawings.

The following description will be made with respect to water-soluble photochromic compounds (formula 12) for labeling biomolecules, which comprise photochromic molecules represented by formula 3, among the water-soluble photochromic compounds for labeling biomolecules, which are represented by formula 1, but the present invention is not limited thereto and can be applied to all the above-described photochromic molecules.

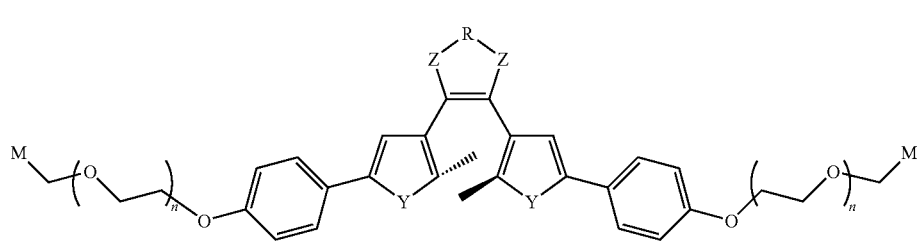

[Formula 12]

wherein R is a bond or a $C_1$-$C_3$ alkylene group which is unsubstituted or substituted with an oxygen or fluorine atom, Y is independently an oxygen, nitrogen or sulfur atom, Z is a methylene group or a carbonyl group, which are unsubstituted or substituted with fluorine, M is a functional group binding selectively to biomolecules, and n is an integer ranging from 1 to 100.

In the present invention, the functional group (M) binding to biomolecules is preferably selected from the group consisting of a carboxyl group, a carboxyl acid derivative (C(=O)—Cl, C(=O)—Br, or C(=O)—O-succinimide), an isocyanate group, an isothiocyanate group, an amine group, a thiol group, a hydroxyl group, an iodoacetamino group, an α-haloacetyl group and a maleimide group.

In the present invention, the biomolecules include nucleic acids, proteins, saccharides, lipids, peptides, nucleotides, metabolic intermediates, metabolic enzymes, hormones, neurotransmitters and the like.

The inventive water-soluble photochromic compounds for labeling biomolecules, which are represented by formula 12, are prepared by allowing a diarylethene compound, having a hydroxyl group at both ends thereof and represented by the following formula 13, to react with an end-modified oligo (ethylene glycol) in the presence of a base, so as to prepare a water-soluble intermediate represented by the following formula 14, and then deprotecting and activating the end groups of the prepared intermediate.

carboxylic acid derivatives modified with N-hydroxysuccinic acid imide (N-hydroxysulfo-succinic acid imide) using EDC (1-ethyl-3-(3-dimethylaminopropyl)carbodimide)/NHS (N-hydroxy succinimide or NHS—$SO_3Na$). In this case, when hydroxysulfosuccinic acid imide (NHS—$SO_3Na$) is used instead of N-hydroxysuccinic acid imide (NHS), a final product having increased water solubility can be obtained, and the amine group can be linked to DNA having a thiol end

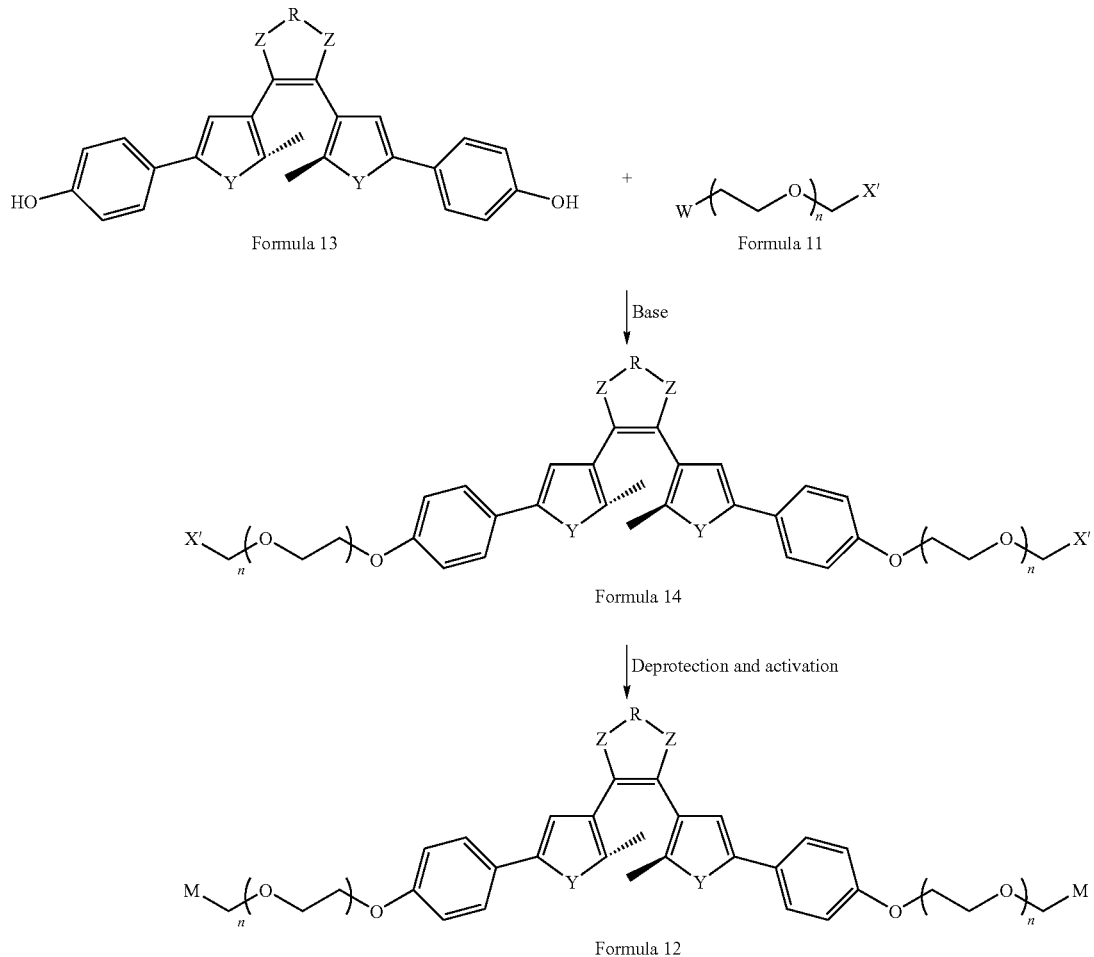

[Reaction Scheme 1]

Formula 13

Formula 11

Base

Formula 14

Deprotection and activation

Formula 12 wherein R, Z, Y, W, X', M and n are as defined above.

The base that is used in the present invention is one or more selected from inorganic bases, such as sodium carbonate, potassium carbonate, cesium carbonate, sodium hydrogen carbonate, potassium hydrogen carbonate, sodium hydroxide or potassium hydroxide, and organic bases, such as triethylamine, DBU, DABCO, DMAP or Proton Sponge, and a solvent usable in the present invention is acetonitrile, acetone, methanol, tetrahydrofuran, dioxane, dimethylacetamide, dimethylformamide, N-methylpyrrolidone, dimethylsulfoxide or the like.

Among the end groups of the compounds represented by formula 12, the carboxyl group can be obtained through ester hydrolysis, and the amine group can be obtained through azide reduction. Also, the carboxyl group can easily react with the amine group of proteins or peptides by forming group or to a protein containing cystein on the surface thereof by allowing it to react with maleic anhydride so as to form maleimide.

Specifically, as shown in FIG. 1, the inventive water-soluble photochromic compounds represented by formula 1 can be easily labeled to amine- or thiol-containing nucleic acids (DNA or RNA) or proteins using a functional group (M in FIG. 1) that reacts selectively with amine or thiol.

Also, the fluorescence switching compounds according to the present invention include not only the fluorescence switching compounds represented by formula 2, but also biomolecule-labeling water-soluble photochromic compounds containing fluorescent substances (in which K is a fluorescent substance or an L-M-fluorescent substance), among the biomolecule-labeling water-soluble photochromic compounds represented by formula 1. The term "fluorescence switching compound" refers to a compound that is obtained by synthesizing a photochromic molecule and a fluorescent substance into one molecule so as to be able to switch fluorescence by the structural change of the photochromic substance.

Figure 2:
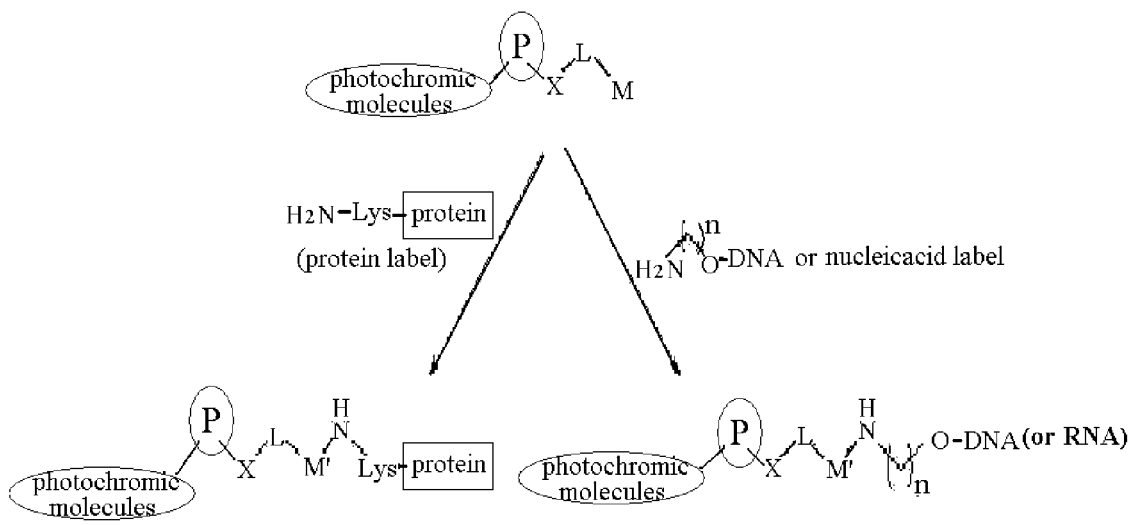
FIG. 2 schematically shows a method of labeling biomolecules with fluorescence switching compounds according to the present invention.

As shown in FIG. 2, the fluorescence switching compounds according to the present invention can be introduced into proteins, nucleic acids or the like, because they have an activated functional group introduced into the end of the molecule, such that they can easily react with, for example, proteins or nucleic acids substituted with amine. Once the fluorescence switching compound is introduced into biomolecules, it can emit or block fluorescence by irradiating light of specific wavelengths.

Figure 3:
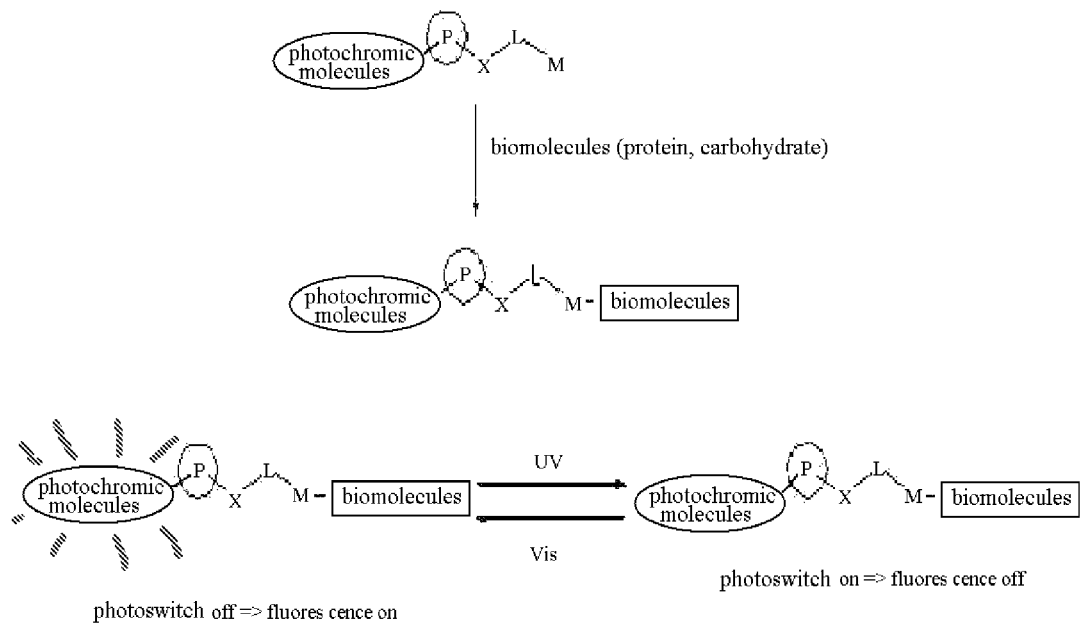
FIG. 3 schematically shows a method of detecting biomolecules using fluorescence switching compounds according to the present invention.

As shown in FIG. 3, when biomolecules labeled with the fluorescence switching compound are irradiated with UV light (354 nm), fluorescence cannot be observed, because the photochromic molecule absorbs light of 550-650 nm, and thus absorbs light emitted from the fluorescent substance. However, when biomolecules labeled with the fluorescence switching compounds are irradiated with visible light (~600 nm), light emitted from the fluorescent substance can be detected, because the photochromic molecule loses the property of absorbing visible light.

In the present invention, when the photochromic molecule is irradiated with UV light having a 290-nm wavelength, it becomes a closed form and is colored, and when it is irradiated with light having a wavelength of 580-590 nm, it becomes an open form and loses the color. Meanwhile, the fluorescent substances according to the present invention have excitation and emission wavelengths of 546 nm and 576 nm for Alexa545, 555 nm and 580 nm for Alexa555, 540 nm and 580 nm for Bodipy TMR, 550 nm and 570 nm for Cy3, 500 nm and 575 nm for DY500, 580 nm and 590 nm for Rhodamin Red-X, and 550 nm and 590 nm for Spectrum orange.

As described above, in the present invention, the excitation wavelength of the fluorescent substance contained in the fluorescence switching compound differs from the wavelength of light inducing the reaction of the photochromic molecule, and thus the fluorescent substance and the photochromic molecule are not influenced by each other.

As shown in the following reaction scheme 2, the method for preparing the fluorescence switching compounds according to the present invention comprises allowing a diarylethene compound, having hydroxyl groups at both ends thereof and represented by the following formula 13, to react with an end-modified oligo(ethylene glycol) represented by the following formula 11 in the presence of a base so as to prepare a water-soluble intermediate, substituted with the hydroxyl group (—OH) at only one end and represented by the following formula 15, and then allowing the hydroxyl group at the other end to react with the radical W of a compound represented by the following formula 16 so as to prepare an intermediate represented by the following formula 17. The end group X' of the intermediate represented by formula 17 is deprotected, and then the hydroxyl group at the other end is allowed to react with a linker having an azido group (—N$_3$). Then, the azido group is reduced to amine, and then a fluorescent substance is introduced into the compound, thus preparing a fluorescence switching compound represented by the following formula 18. Because M of the compound represented by formula 18 consists of either N-hydroxysuccinic acid imide (or N-hydroxysulfosuccinic acid imide) of carboxylic acid, or maleimide, it reacts with the amine or cysteine residue of proteins or peptides to label the biomolecules.

The base that is used in the present invention is one or more selected from among inorganic salts, such as sodium carbonate, potassium carbonate, cesium carbonate, sodium hydrogen carbonate, potassium hydrogen carbonate, sodium hydroxide or potassium hydroxide, and organic salts, such as triethylamine, DBU, DABCO, DMAP or Proton Sponge, and the solvent usable in the present invention is acetonitrile, acetone, methanol, tetrahydrofuran, dioxane, dimethylacetamide, dimethylformamide, N-methylpyrrolidone, dimethylsulfoxide or the like.

The fluorescent substance that is used in the present invention is one or more selected from the group consisting of, but not limited to, Alexa 555, bodipy TMR, Cy3, DY500, Rhodamine red-X, Spectrum orange, Fluorescein isothiocyanate (FITC) or Tetramethylrhodamine isothiocyanate (TRITC), Alexa fluor, Texas red, Tetramethylrhodamine, Cascade blue, DAPI (4',6-diamidino-2-phenylindole), coumarine, Lucifer yellow and Dansylamide.

[Reaction Scheme 2]

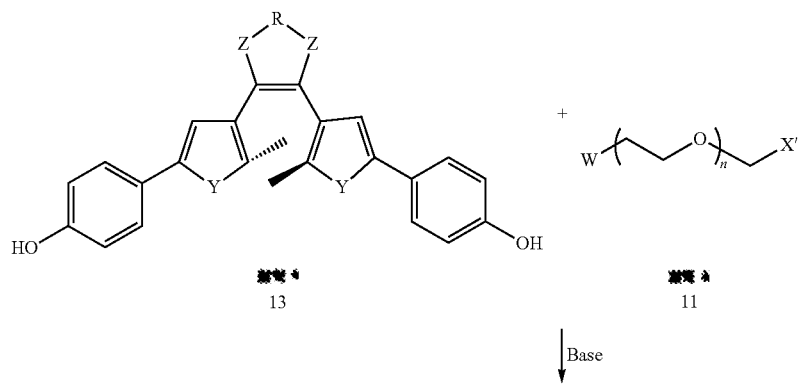

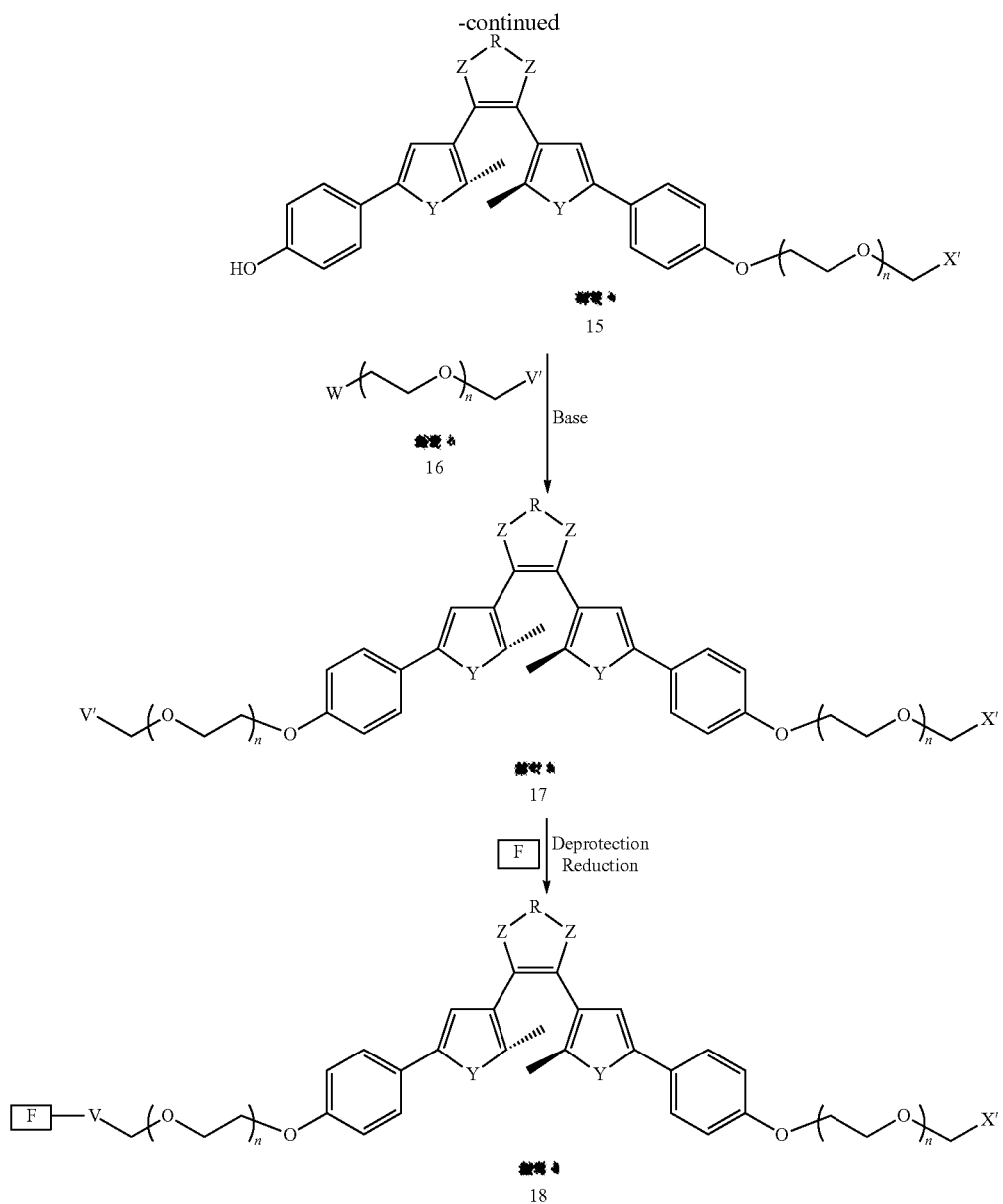
wherein V' is $N_3$, V is $NH_2$, F is a fluorescent substance, and R, Z, Y, W, X', M and n are defined as above.

[Reaction Scheme 3]
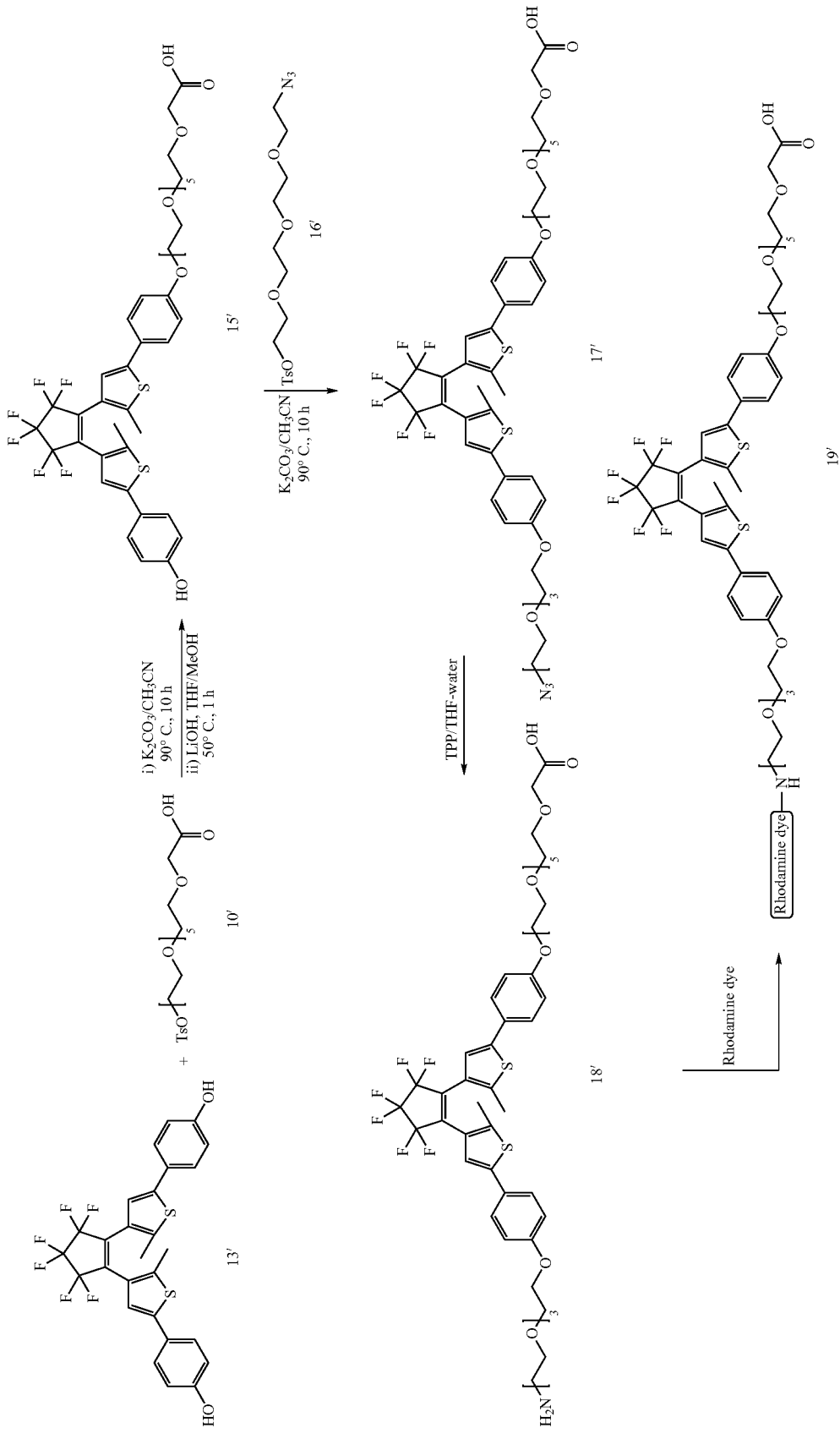

The above reaction scheme 3 illustrates an example of a method for preparing the fluorescence switching compounds according to the present invention. As shown in reaction scheme 3, the preparation method comprises allowing a compound 13' to react with a compound 10' to synthesize a compound 15' substituted with the hydroxyl group at only one end, and then allowing the hydroxyl group at the other end to react with a linker having an azido group (—N₃), thus preparing a compound 17'. The azido group of the prepared compound 17' is reduced to amine to obtain a compound 18', and then a fluorescent substance is then introduced into the compound 18', thus preparing a fluorescence switching compound 19'.

EXAMPLES

Hereinafter, the present invention will be described in further detail with reference to examples. It will be obvious to those skilled in the art that these examples are illustrative purpose only and are not to be construed to limit the scope of the present invention, because these examples can be modified into other various forms.

Example 1

Preparation of Water-Soluble Photochromic Compound for Labeling Biomolecules 1-1: Preparation of Water-Soluble Photochromic Compound As shown in the following reaction scheme 4, 0.5 g (0.9 mmol) of compound 1 and 0.67 g (1.9 mmol) of compound 2 were dissolved in 40 ml of acetonitrile, and 0.37 g (2.7 mmol) of potassium carbonate was added thereto. The mixture was stirred at 90° C. for 10 hours. After the solvent of the stirred mixture was removed under reduced pressure, the residue was dissolved in 100 ml of methylene chloride, and the organic layer was washed three times with distilled water. The organic layer of the mixture was dried over anhydrous magnesium sulfate and filtered, and the filtrate was concentrated under reduced pressure. The residue was purified by silica column chromatography (ethyl acetate), thus preparing 0.75 g (yield: 80%) of compound 3 having water solubility. H-NMR data of the compound 3 prepared above is as follows:

[$^1$H-NMR (300 MHz, CDCl₃): δ 1.94 (s, 3H: S—C—CH₃), 3.67-3.74 (m, 15H: 12H for —CH₂—(—CH₂—O—CH₂)₂—CH₂—O—CH₂—COO and 3H for —CH₂—COO—CH₃), 3.87 (t, J=5.1 Hz 2H: Ar—O—CH₂—CH₂—O), 4.13-4.16 (m, 4H: 2H for Ar—O—CH₂—CH₂—O and 2H for —CH₂—CH₂—O—CH₂—COO—CH₃), 6.92 (d, J=8.7 Hz, 2H: —S—C—C—CH₂—CH₂—C—O—), 7.1 (s, 1H: —S—C—CH—C—), 7.44 (d, J=8.1 Hz, 2H: —S—C—C—CH₂—CH₂—C—O—)]

[Reaction Scheme 4]

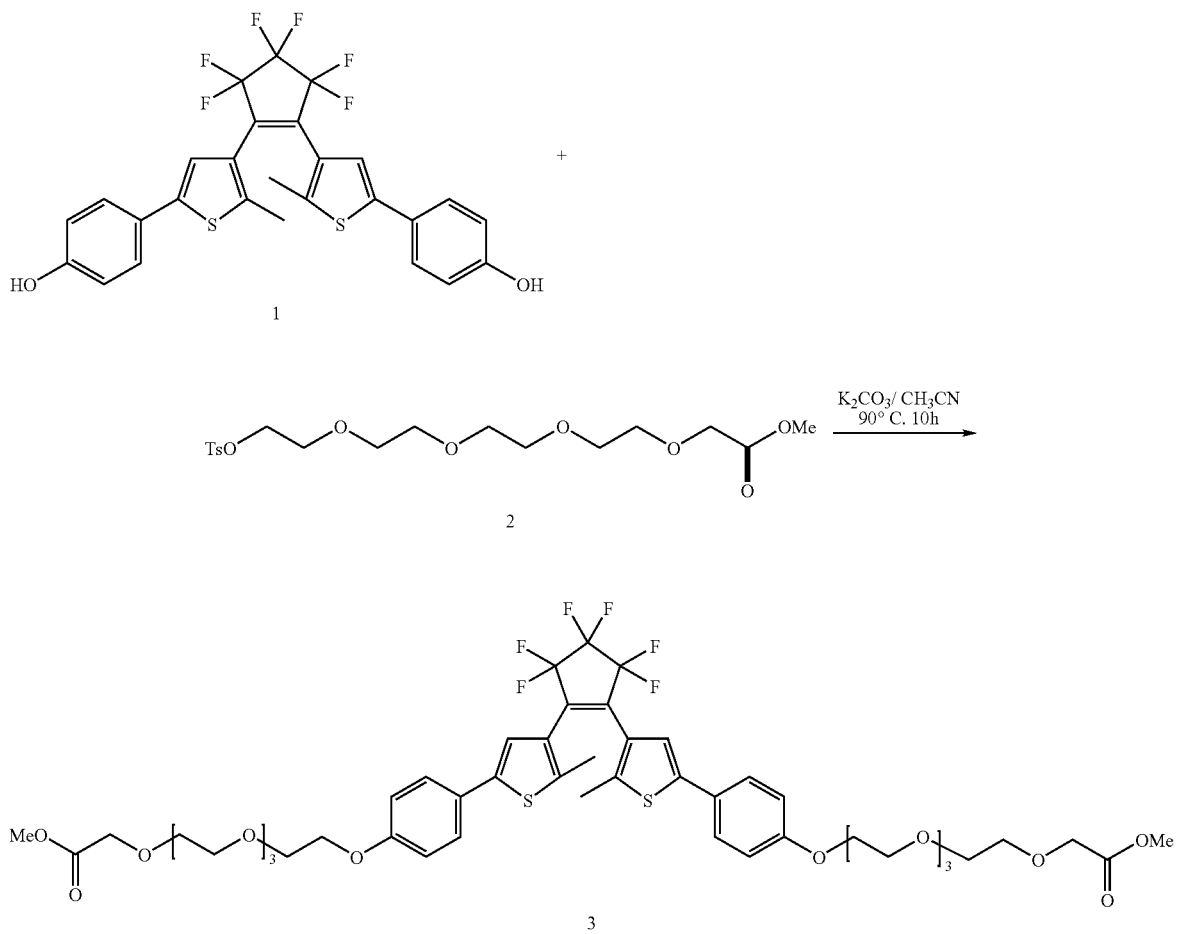

1-2: Preparation of Water-Soluble Photochromic Compound having Deprotected End Groups As shown in the following reaction scheme 5, 0.45 g (0.4 mmole) of compound 3 and 0.1 ml (2.1 mmol) of 1N LiOH aqueous solution were mixed with each other in a mixture of methanol and THF (1:4) and stirred at 50° C. for one hour. The solvent of the stirred mixture was removed under reduced pressure, and the residue was dissolved in a 1N hydrochloric acid solution and extracted with ethyl acetate. The extract was washed twice with water. The resulting material was dried over anhydrous magnesium sulfate and filtered, and the filtrate was concentrated under reduced pressure, thus preparing 0.36 g (yield: 80%) of compound 4 having deprotected end groups. H-NMR data of the compound 4 prepared above is as follows:

[$^1$H-NMR (300 MHz, CDCl$_3$): δ 1.96(s, 3H: S—C—CH$_3$), 3.67-3.74 (m, 12H: —CH$_2$—(—CH$_2$—O—CH$_2$)$_2$—CH$_2$—O—CH$_2$—COOH), 3.87 (t, J=5.1 Hz 2H: Ar—O—CH$_2$—CH$_2$—O), 4.11-4.18 (m, 4H: 2H for Ar—O—CH$_2$—CH$_2$—O and 2H for —CH$_2$—CH$_2$—O—CH$_2$—COOH), 6.92 (d, J=8.9 Hz, 2H: —S—C—C—CH$_2$—CH$_2$—C—O—), 7.13 (s, 1H: —S—C—CH—C—), 7.44 (d, J=8.7 Hz, 2H: —S—C—C—CH$_2$—CH$_2$—C—O—)]

[Reaction Scheme 5]

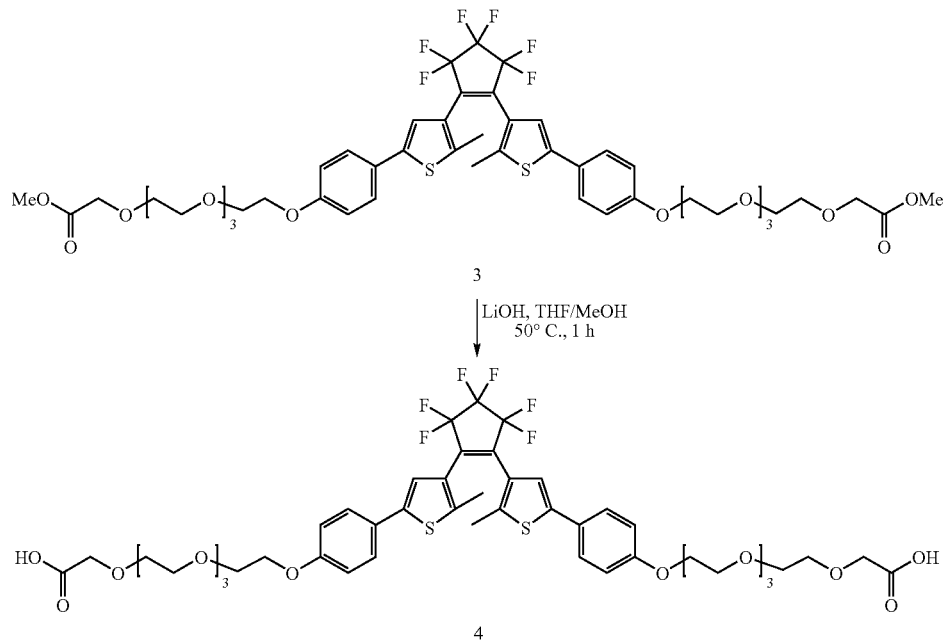

1-3: Preparation of Water-Soluble Photochromic Compound for Labeling Biomolecules As shown in the following reaction scheme 6, 0.1 g (0.09 mmole) of compound 4 was dissolved in 15 ml of methylene chloride, and then 0.12 g (0.48 mmole) of N,N'-disuccinimidyl carbonate and 40 μl (0.3 mmole) of triethylamine were added thereto. The solution was stirred at room temperature for 3 hours. The stirred solution was placed in a separatory funnel and washed with methylene chloride and 10% hydrochloric acid and sodium chloride aqueous solution. Then, the solution was dried over anhydrous magnesium sulfate and filtered, and filtrate was concentrated under reduced pressure, thus preparing 80 mg (yield: 68%) of a water-soluble photochromic compound (compound 5) for labeling biomolecules. H-NMR data of the compound 5 prepared above is as follows:

[$^1$H-NMR (300 MHz, CDCl$_3$): δ 1.94 (s, 3H: S—C—CH$_3$), 2.83 (s, 4H: N—CO—CH$_2$—CH$_2$—CO), 3.66-3.80 (m, 12H: —CH$_2$—[—CH$_2$—O—CH$_2$]$_2$—CH$_2$—O—CH$_2$—COO), 3.87(t, J=3.6 Hz 2H: Ar—O—CH$_2$—CH$_2$—O), 4.15 (t, J=4.5 Hz 2H: Ar—O—CH$_2$—CH$_2$—O), 4.51 (s, 2H: —CH$_2$—CH$_2$—O—CH$_2$—COO—N—), 6.92 (d, J=8.9 Hz, 2H: —S—C—C—CH$_2$—CH$_2$—C—O—), 7.13 (s, 1H: —S—C—CH—C—), 7.44 (d, J=8.7 Hz, 2H: —S—C—C—CH$_2$—CH$_2$—C—O—)]

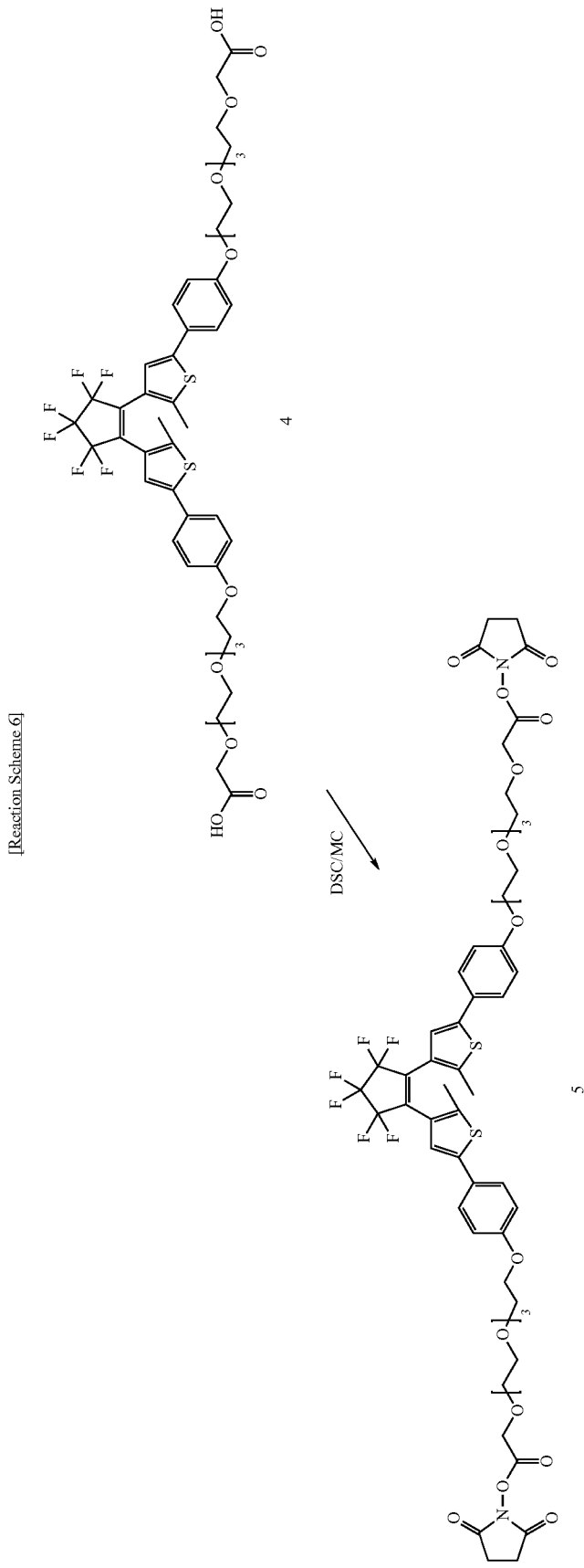

Example 2

Preparation of Strip for Antibody Detection

Figure 4:
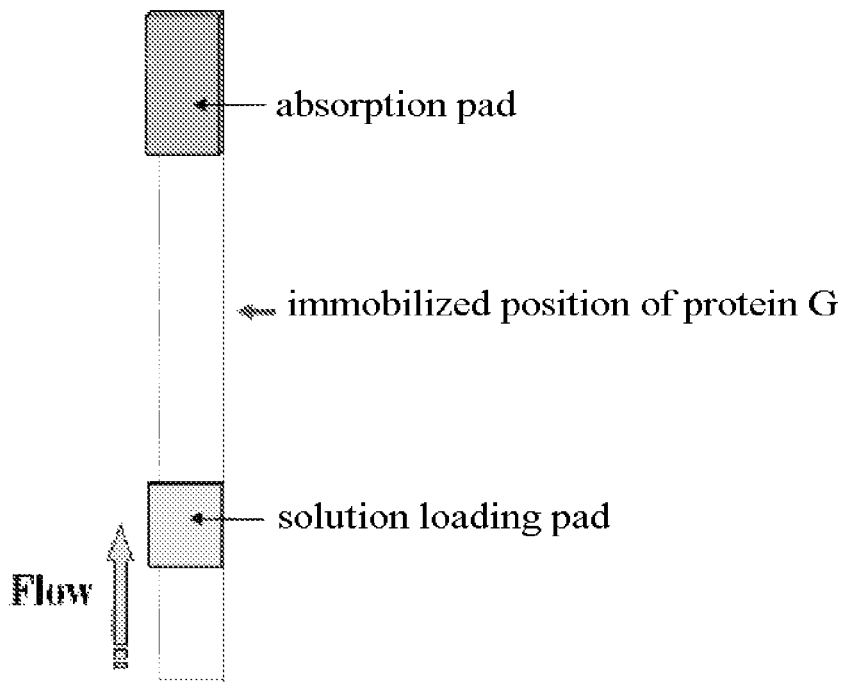
FIG. 4 shows a strip for detecting antibodies using water-soluble photochromic compounds for labeling biomolecules according to the present invention.

In order to prepare a strip for detecting antibodies binding to protein G, as shown in FIG. 4, 50 μl of a PBS buffer containing 0.5 mg/ml of protein G (12.5 kDa) was sprayed onto a 30-cm strip in the form of lines using a dispenser, and then the strip was dried at room temperature for 30 minutes. The strip onto which protein G has been physically adsorbed and immobilized was uniformly cut to a size of 3.3 mm.

Experimental Example 1

Experiment of Antibody Detection using the Water-Soluble Photochromic Compound for Labeling Biomolecules In order to test selective binding between IgG and protein G, a sample was prepared by labeling IgG with the water-soluble photochromic compound for labeling biomolecules prepared in Example 1, and a control group sample was prepared by labeling BSA with the same photochromic compound. IgG used in the labeling was used at varying concentrations of 1.6, 3.3 and 4.9 nmol, and the concentration of BSA was 4.9 nmol. The labeled proteins (IgG—PC and BSA—PC) were sufficiently dialyzed before use in order to remove an excess photochromic compound. 10 μl of each of the prepared IgG—PC and BSA—PC was loaded onto the strip prepared in Example 2, and then the lower end of the strip was immersed in 25 μl of PBS buffer (pH 7.4) for 10 minutes, such that each of the samples could smoothly flow to the absorption pad of the strip. After completion of all such operations, the strip was irradiated with UV light (365 nm, 7 mW) for 2 minutes, and then the band at the position of protein G was examined.

Figure 5:
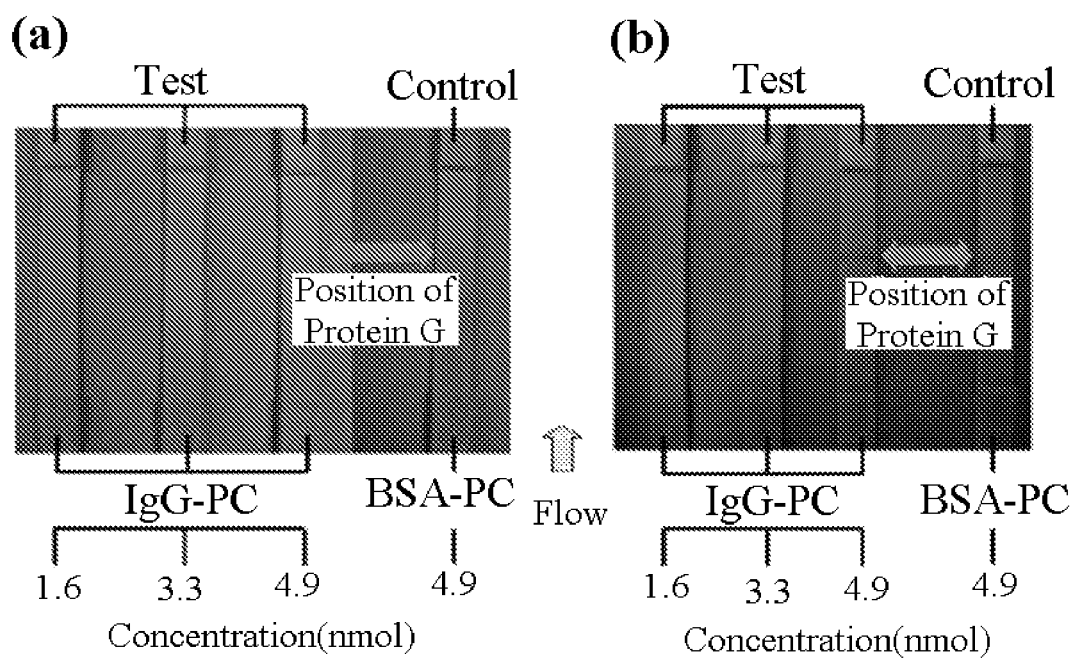
FIG. 5 shows that IgG was detected using a strip sensor comprising water-soluble photochromic compounds for labeling biomolecules according to the present invention.

As a result, as shown in FIG. 5(a), before the strip was irradiated with UV light, a visually observable band was not shown. However, as shown in FIG. 5(b), after the strip was irradiated with UV light, a blue band was shown, suggesting that IgG—PC was bound selectively to the position of the immobilized protein G. The protein band was visually observable, showing high sensitivity and almost proportional to the concentration of the sample.

INDUSTRIAL APPLICABILITY

As described above, when the inventive water-soluble photochromic compounds for labeling biomolecules are used to detect biomolecules, undesired background signals will be reduced, thus improving detection sensitivity. In addition, because the inventive water-soluble photochromic compounds exhibit the color corresponding to the wavelength of visible light, they allow signals to be easily detected not only with an UV-VIS spectrophotometer but also visually. Moreover, because the photochromic molecules labeled to biomolecules show a color change by light of specific wavelengths, they generate signals by inducing a color change by light only at a desired time and space, thus greatly improving the detection sensitivity in samples. Accordingly, the inventive photochromic compounds can be used in sensors for diagnosing diseases.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. Water-soluble photochromic compounds for labeling biomolecules, which are represented by the following formula 1:

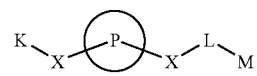

[Formula 1]

wherein, P is a photochromic molecule selected from the group consisting of compounds represented by the following formulas 3-10 and isomers thereof, L is $(CH_2CH_2O)_n$, where n is an integer ranging from 1 to 100, M is a functional group binding selectively to biomolecules, K is a fluorescent substance or an L, L-M or L-M-fluorescent substance, and X is selected from the group consisting of O, S, NH, and $CH_2$,

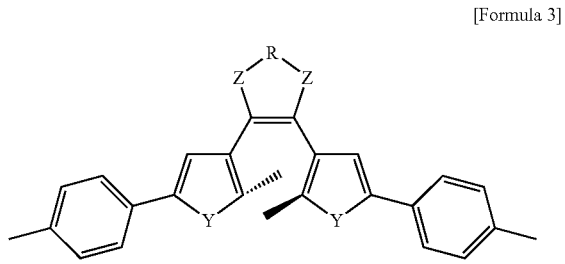

[Formula 3]

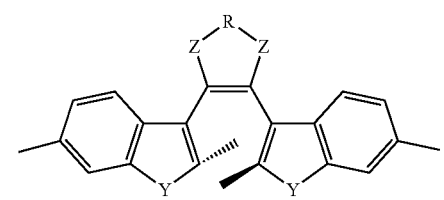

[Formula 4]

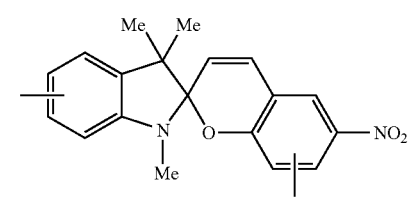

[Formula 5]

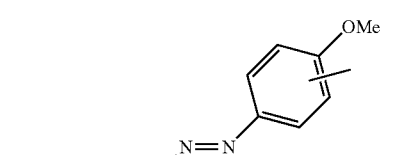

[Formula 6]

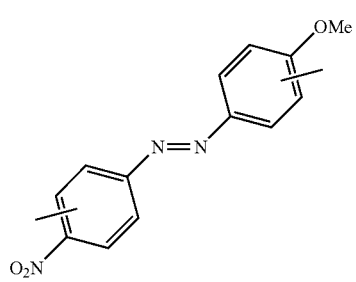

[Formula 7]

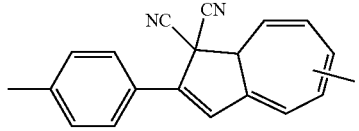

-continued

[Formula 8]
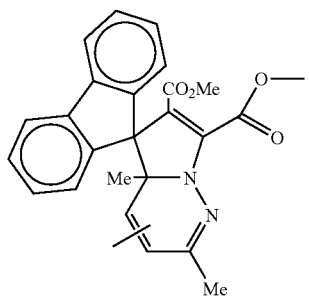

[Formula 9]
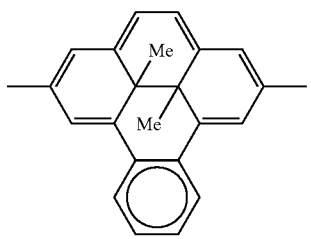

[Formula 10]
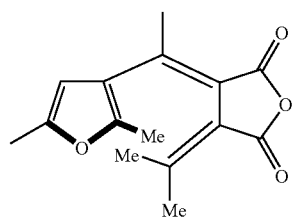

wherein, in the formula 3 and 4, R is a bond or a $C_1$-$C_3$ alkylene group which is unsubstituted or substituted with an oxygen or fluorine atom, Y is independently an oxygen, nitrogen or sulfur atom, and Z is a methylene group or a carbonyl group, which are unsubstituted or substituted with fluorine.

2. The water-soluble photochromic compounds for labeling biomolecules according to claim 1, wherein the functional group (M) binding to biomolecules is selected from the group consisting of a carboxyl group, a carboxyl acid derivative selected from the group consisting of C(=O)—Cl, C(=O)—Br, and C(=O)—O-succinimide, an isocyanate group, an isothiocyanate group, an amine group, a thiol group, a hydroxyl group, an iodoacetamino group, an α-haloacetyl group and a maleimide group.

3. The water-soluble photochromic compounds for labeling biomolecules according to claim 1, wherein the fluorescent substance is one or more selected from the group consisting of Alexa 555, Bodipy TMR, Cy3, DY500, Rhodamine red-X, Spectrum orange, Fluorescein isothiocyanate (FITC) or Tetramethylrhodamine isothiocyanate (TRITC), Alexa fluor, Texas red, Tetramethylrhodamine, Cascade blue, DAPI (4',6-diamidino-2-phenylindole), Coumarine, Lucifer yellow and Dansylamide.

4. Water-soluble photochromic compounds represented by the following formula 12:

wherein, R is a bond or a $C_1$-$C_3$ alkylene group which is unsubstituted or substituted with an oxygen or fluorine atom, Y is independently an oxygen, nitrogen or sulfur atom, Z is a methylene group or a carbonyl group which are unsubstituted or substituted with fluorine, M is a functional group binding selectively to biomolecules, and n is an integer ranging from 1 to 100.

5. The water-soluble photochromic compounds for labeling biomolecules according to claim 4, wherein the functional group (M) binding to biomolecules is selected from the group consisting of a carboxyl group, a carboxyl acid derivative selected from the group consisting of C(=O)—Cl, C(=O)—Br, and C(=O)—O-succinimide, an isocyanate group, an isothiocyanate group, an amine group, a thiol group, a hydroxyl group, an iodoacetamino group, an α-haloacetyl group and a maleimide group.

6. A method for preparing water-soluble photochromic compounds for labeling biomolecules, which are represented by formula 1:

[Formula 1]
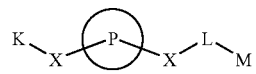

wherein, P is a photochromic molecule selected from the group consisting of compounds represented by the following formulas 3-10 and isomers thereof, L is $(CH_2CH_2O)_n$, where n is an integer ranging from 1 to 100, M is a functional group binding selectively to biomolecules, K is a fluorescent substance or an L, L-M or L-M-fluorescent substance, and X is selected from the group consisting of O, S, NH, and $CH_2$

[Formula 3]
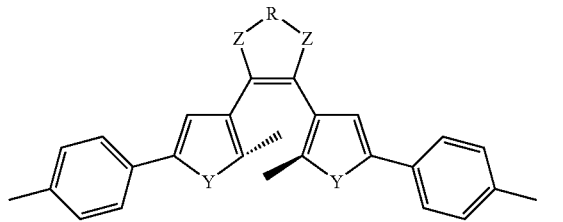

[Formula 4]
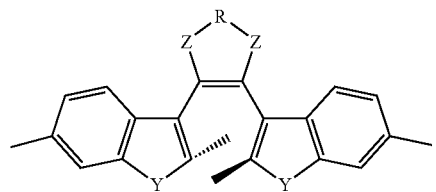

[Formula 5]
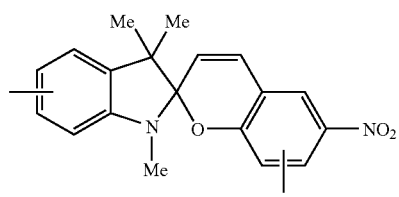

[Formula 12]
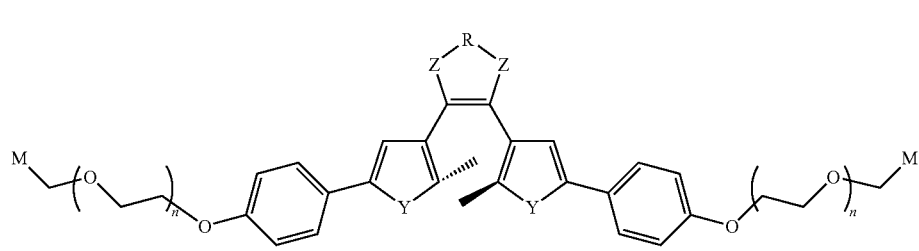

[Formula 6]

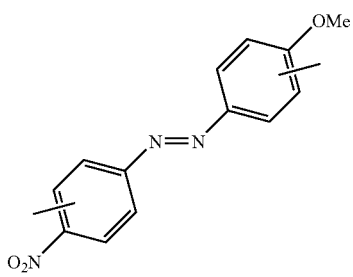

[Formula 7]

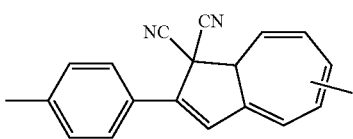

[Formula 8]

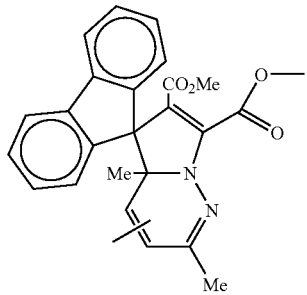

[Formula 9]

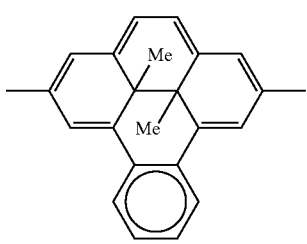

[Formula 10]

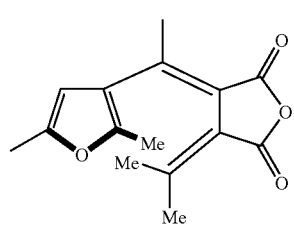

wherein, in the formula 3 and 4, R is a bond or a $C_1$-$C_3$ alkylene group which is unsubstituted or substituted with an oxygen or fluorine atom, Y is independently an oxygen, nitrogen or sulfur atom, and Z is a methylene group or a carbonyl group, which are unsubstituted or substituted with fluorine, the method comprising the steps of:

(a) allowing a photochromic molecule (P) containing, at one end or both ends thereof, a functional group selected from the group consisting of a hydroxyl group (—OH), a thiol group (—SH), a methyl group (—CH$_3$), an amine group (—NH$_2$) and combinations thereof to react with an end-modified oligo(ethylene glycol) represented by the following formula 11 in the presence of a base, thus preparing an end-group-protected intermediate represented by the following formula 20:

[Formula 11]

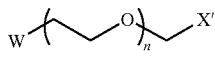

wherein W is tosylate (—OTs), mesylate (—OMs) or triflate (—OTf), X' is carboxylic acid alkyl ester (C(=O)OR', R'=$C_1$-$C_4$ alkyl), azide (N$_3$) or carbamate (NHC(O)OR), where R is t-butyl, benzyl or methyl, and n is an integer ranging from 1 to 100,

[Formula 20]

wherein P is a photochromic molecule, X' is carboxylic acid alkyl ester (C(=O)OR', R'=$C_1$-$C_4$ alkyl), azide (N$_3$) or carbamate (NHC(O)OR), where R is t-butyl, benzyl or methyl, and n is an integer ranging from 1 to 100;

(b) subjecting the end group-protected intermediate represented by formula 20 to ester hydrolysis or azide reduction in the presence of a base and solvent, thus preparing a carboxylic acid intermediate or an amine intermediate; and (c) either allowing the prepared carboxylic acid intermediate to react with NHS/EDC or NHS-SO$_3$Na so as to convert the carboxylic acid intermediate to N-hydroxysuccinic acid imide or N-hydroxysulfosuccinic acid imide derivatives as photochromic compounds for labeling biomolecules, or allowing the prepared amine intermediate to react with a compound selected from the group consisting of carbonyldimidazol, carbonyldisuccinate, phosgene and ammonium thiocyanate so as to convert the amine intermediate to isocyanate or isothiocyanate derivatives as photochromic compounds for labeling biomolecules.

7. The method for preparing water-soluble photochromic compounds for labeling biomolecules according to claim 6, wherein the functional group (M) binding to biomolecules is selected from the group consisting of a carboxyl group, a carboxyl acid derivative selected from the group consisting of C(=O)—Cl, C(=O)—Br, and C(=O)—O-succinimide, an isocyanate group, an isothiocyanate group, an amine group, a thiol group, a thiol group, a hydroxyl group, an iodoacetamino group, an α-haloacetyl group and a maleimide group.

8. The method for preparing water-soluble photochromic compounds for labeling biomolecules according to claim 6, wherein the base is selected from the group consisting of sodium carbonate, potassium carbonate, cesium carbonate, sodium hydrogen carbonate, potassium hydrogen carbonate, sodium hydroxide, potassium hydroxide, triethylamine, DBU, DABCO, DMAP and Proton Sponge.

9. The method for preparing water-soluble photochromic compounds for labeling biomolecules according to claim 6, wherein the solvent is selected from the group consisting of acetonitrile, acetone, methanol, tetrahydrofuran, dioxane, dimethylacetamide, dimethylformamide, N-methylpyrrolidone, dimethylsulfoxide, and a mixture thereof.

10. The method for preparing water-soluble photochromic compounds for labeling biomolecules according to claim 6, which additionally comprises a step of linking a fluorescent substance to the water-soluble photochromic compounds for labeling biomolecules prepared in step (b).

11. The method for preparing water-soluble photochromic compounds for labeling biomolecules according to claim 6, wherein the fluorescent substance is one or more selected from the group consisting of Alexa 555, Bodipy TMR, Cy3, DY500, Rhodamine red-X, Spectrum orange, Fluorescein isothiocyanate (FITC) or Tetramethylrhodamine isothiocyanate (TRITC), Alexa fluor, Texas red, Tetramethylrhodamine, Cascade blue, DAPI (4',6-diamidino-2-phenylindole), Coumarine, Lucifer yellow and Dansylamide.

12. A method for preparing water-soluble photochromic compounds for labeling biomolecules, which are represented by formula 12:

[Formula 12]

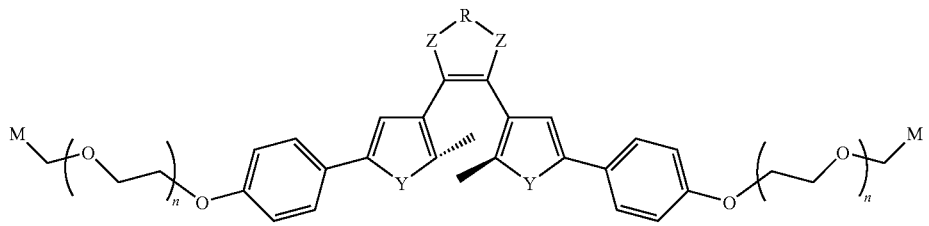

wherein, R is a bond or a $C_1$-$C_3$ alkylene group which is unsubstituted or substituted with an oxygen or fluorine atom, Y is independently an oxygen, nitrogen or sulfur atom, Z is a methylene group or a carbonyl group, which are unsubstituted or substituted with fluorine, M is a functional group binding selectively to biomolecules, and n is an integer ranging from 1 to 100, the method comprising the steps of:

(a) allowing a photochromic molecule, containing a hydroxyl group (—OH) at both ends thereof and represented by the following formula 3', to react with an end-modified oligo(ethylene glycol) represented by the following formula 11 in the presence of a base, thus preparing an end group-protected intermediate represented by the following formula 14:

[Formula 3']

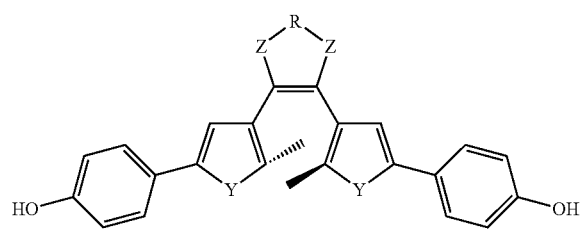

wherein R is a bond or a $C_1$-$C_3$ alkylene group which is unsubstituted or substituted with an oxygen or fluorine atom, Y is independently an oxygen, nitrogen or sulfur atom, Z is a methylene group or a carbonyl group, which are unsubstituted or substituted with fluorine,

[Formula 11]

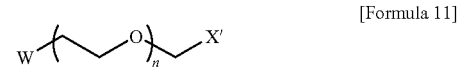

wherein, W is tosylate (—OTs), mesylate (—OMs) or triflate (—OTf), X' is carboxylic acid alkyl ester (C(=O)OR', R'=$C_1$-$C_4$ alkyl), azide ($N_3$) or carbamate (NHC(O)OR), where R is t-butyl, benzyl or methyl, and n is an integer ranging from 1 to 100, wherein, R is a bond or a $C_1$-$C_3$ alkylene group which is unsubstituted or substituted with an oxygen or fluorine atom, Y is independently an oxygen, nitrogen or sulfur atom, Z is a methylene group or a carbonyl group, which are unsubstituted or substituted with fluorine, X' is carboxylic acid alkyl ester (C(=O)OR', R'=$C_1$-$C_4$ alkyl), azide ($N_3$) or carbamate (NHC(O)OR), where R is t-butyl, benzyl or methyl, and n is an integer ranging from 1 to 100;

(b) subjecting the end group-protected intermediate represented by formula 14 to ester hydrolysis or azide reduction in the presence of a base and solvent, thus preparing a carboxylic acid intermediate or an amine intermediate; and (c) either allowing the prepared carboxylic acid intermediate to react with NHS/EDC or NHS-$SO_3$Na so as to convert the carboxylic acid intermediate to N-hydroxysuccinic acid imide or N-hydroxysulfosuccinic acid imide derivatives as photochromic compounds for labeling biomolecules, or allowing the prepared amine intermediate to react with a compound selected from the group consisting of carbonyldimidazol, carbonyldisuccinate, phosgene and ammonium thiocyanate so as to convert the amine intermediate to isocyanate or isothiocyanate derivatives as photochromic compounds for labeling biomolecules.

13. The method for preparing water-soluble photochromic compounds for labeling biomolecules according to claim 12, wherein the functional group (M) binding to biomolecules is selected from the group consisting of a carboxyl group, a carboxyl acid derivative selected from the group consisting of C(=O)—Cl, C(=O)—Br, and C(=O)—O-succinimide an isocyanate group, an isothiocyanate group, an amine group, a thiol group, a hydroxyl group, an iodoacetamino group, an α-haloacetyl group and a maleimide group.

14. The method for preparing water-soluble photochromic compounds for labeling biomolecules according to claim 12, wherein the base is selected from the group consisting of sodium carbonate, potassium carbonate, cesium carbonate, sodium hydrogen carbonate, potassium hydrogen carbonate, sodium hydroxide, potassium hydroxide, triethylamine, DBU, DABCO, DMAP and Proton Sponge

15. The method for preparing water-soluble photochromic compounds for labeling biomolecules according to claim 12, wherein the solvent is selected from the group consisting of

[Formula 14]

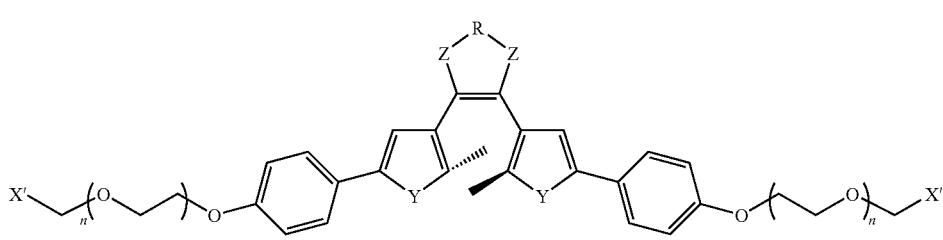

acetonitrile, acetone, methanol, tetrahydrofuran, dioxane, dimethylacetamide, dimethylformamide, N-methylpyrrolidone, dimethylsulfoxide, and a mixture thereof.

16. The method for preparing water-soluble photochromic compounds for labeling biomolecules according to claim 12, which additionally comprises a step of linking a fluorescent substance to the water-soluble photochromic compounds for labeling biomolecules prepared in step (b).

17. The method for preparing water-soluble photochromic compounds for labeling biomolecules according to claim 16, wherein the fluorescent substance is one or more selected from the group consisting of Alexa 555, Bodipy TMR, Cy3, DY500, Rhodamine red-X, Spectrum orange, Fluorescein isothiocyanate (FITC) or Tetramethylrhodamine isothiocyanate (TRITC), Alexa fluor, Texas red, Tetramethylrhodamine, Cascade blue, DAPI (4',6-diamidino-2-phenylindole), Coumarine, Lucifer yellow and Dansylamide.

18. A method for labeling or detecting biomolecules, which is characterized by using the water-soluble photochromic compounds for labeling biomolecules of claim 1.

19. A method for labeling or detecting biomolecules, which is characterized by using the water-soluble photochromic compounds for labeling biomolecules of claim 4.

* * * * *

UNITED STATES PATENT AND TRADEMARK OFFICE
CERTIFICATE OF CORRECTION

PATENT NO. : 8,415,472 B2
APPLICATION NO. : 12/739601
DATED : April 9, 2013
INVENTOR(S) : Chung et al.

It is certified that error appears in the above-identified patent and that said Letters Patent is hereby corrected as shown below:

Title Page, item (75), line 1, change "Bony Hyun Chung" to --Bong Hyun Chung--

Signed and Sealed this
Twenty-fifth Day of June, 2013

Teresa Stanek Rea
*Acting Director of the United States Patent and Trademark Office*